United States Patent [19]

Yamanaka

[11] Patent Number: 4,825,423
[45] Date of Patent: Apr. 25, 1989

[54] METHOD OF MEASURING MICROCRACK DEPTH

[75] Inventor: Kazushi Yamanaka, Ibaraki, Japan

[73] Assignees: Agency of Industrial Science & Technology; Ministry of International Trade & Industry, both of Tokyo, Japan

[21] Appl. No.: 940,085

[22] Filed: Dec. 10, 1986

[30] Foreign Application Priority Data

Dec. 10, 1985 [JP] Japan ................................ 60-277349

[51] Int. Cl.⁴ .............................................. G01S 9/68
[52] U.S. Cl. ......................................... 367/99; 73/598
[58] Field of Search .................. 364/507; 73/606, 598; 367/118, 119, 124, 99

[56] References Cited

U.S. PATENT DOCUMENTS

| | | | |
|---|---|---|---|
| 2,995,925 | 8/1961 | Worlton | 73/623 |
| 3,165,922 | 1/1965 | Worlton | 73/627 |
| 4,274,288 | 6/1981 | Tittmann et al. | 364/507 X |
| 4,524,621 | 6/1985 | Yamanaka | 73/606 X |
| 4,593,568 | 6/1986 | Telford et al. | 73/623 |

OTHER PUBLICATIONS

R. D. Weglein; "A Model for Predicting Acoustic Material Signatures", Appl. Phys Lett 34(3), Feb. 1, 1979, pp. 179–181.

T. K. Lockett; Lamb and Torsional waves and the use in flaw . . . Ultrasonics, Jan. 1973.

Primary Examiner—Thomas H. Tarcza
Assistant Examiner—Tod R. Swann
Attorney, Agent, or Firm—Oblon, Fisher, Spivak, McClelland & Maier

[57] ABSTRACT

A method of measuring the depth of a microcrack. A sample which has a crack substantially parallel to the surface and slightly inclined is set in the neighborhood of the focal point of a converging acoustic beam, and the depth of a microcrack of the sample irradiated with the beam is measured on the basis of the phenomenon that the reflected wave intensity assumes a minimum value when the product of the crack depth and the frequency of the acoustic wave is equal to a half integral multiple of the velocity of the acoustic waves in the sample.

1 Claim, 6 Drawing Sheets

METHOD OF MEASURING MICROCRACK DEPTH

FIELD OF THE INVENTION AND RELATED ART STATEMENT

This invention relates to a method of non-destructively measuring the depth of subsurface microcracks.

In the measurement of the depth of cracks in materials, there has hitherto been no effective method of detection of cracks whose size and depth from the material surface are both less than 100 $\mu$m. Thus, development of a method of detection using an acoustic microscope has been desired.

To cope with this problem, the present inventor earlier proposed a method of measuring crack depths smaller than wavelength of the acoustic beam used for the measurement by utilizing the relation between Lamb wave velocity and crack depth (Japanese Patent Application SHO 60-97547). This method is useful in that it makes use of the convenience of the acoustic microscope. It is also useful in that it permits measurement of the average value of the crack depth over an area greater than the image resolution. However, since the sample surface is set at a point closer than the focal plane of the microscope, the azimuth resolution is reduced to an extent corresponding to the spread of the beam. Meanwhile, in order to be able to make utmost use of the power of the acoustic microscope, it is desired to be able to obtain quantitative measurement with the same spacial resolution as the image.

OBJECT AND SUMMARY OF THE INVENTION

An object of the invention is to provide a method of measuring microcrack depth capable of carrying out measurement with the same azimuthal resolution as an acoustic image.

In the method of measuring the depth of a microcrack according to the invention, a sample which has a crack substantially parallel to its surface and slightly inclined is set in the neighborhood of the focal point of a converging acoustic beam, and the depth of the microcrack of the sample irradiated with the beam is measured utilizing the phenomenon that the reflected wave intensity assumes a minimum value when the product of the crack depth and the frequency of the acoustic wave is equal to a half integral multiple of the velocity of the acoustic wave through the sample. The reflected wave intensity minimum is produced due to an interference effect wherein the excitation in the sample which satisfies the above condition of a Lamb wave having a very high phase velocity causes a delay in phase of a portion of the incident beam including the axis thereof with respect to the phase of peripheral portions of the beam.

Thus, according to the invention the sample is set in the neighborhood of the focal point of an acoustic beam for the measurement of the crack depth, so that it is possible to obtain measurement of the crack depth using a commercially available acoustic microscope and with the same azimuth resolution as the acoustic image.

BRIEF DESCRIPTION OF THE DRAWINGS

The above and other objects and features of the invention will become more apparent from the following detailed description with reference to the accompanying drawings, wherein.

DETAILED DESCRIPTION OF THE PREFERRED EMBODIMENT

Figure 1:
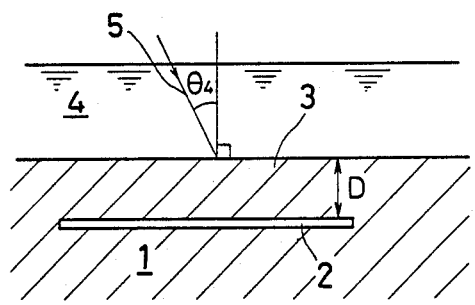
FIG. 1 is an explanatory view showing the method according to the invention.
Figure 2:
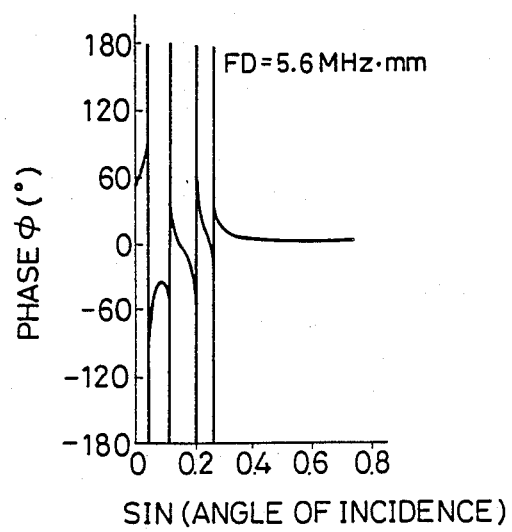
FIG. 2 is a graph showing the dependency of the phase of plane wave reflectivity on the angle of incidence.

FIG. 1 is a schematic view for explaining the principles underlying the invention. Reference numeral 1 designates a sample, numeral 2 a crack, numeral 3 a thin plate-like portion with a thickness D defined between an object surface and the crack 2, and numeral 4 liquid as couplant, which is usually water.

Where even a slight gap accompanies a crack, sound cannot penetrate the crack, and the depth of the crack 2 present in the sample shown in FIG. 2 can be determined from the acoustic characteristics of the water 4 used as the couplant and the thin plate-like portion 3 of thickness D.

The contrast of an acoustic image due to the presence of a crack is determined by the angle of incidence dependency of the amplitude and phase of the reflectivity. Therefore, when an acoustic wave 5 is emitted such that it is incident on the surface of a semi-infinite object (sample) 1 at an angle of $\theta_4$, as shown in FIG. 1, the reflectivity R of the slanted incident plane wave on the plate from the liquid 4 is expressed as $$R = [-AZ_4 + i(A^2 - B^2)] / [(AZ_4 + i(A^2 - B^2)] \tag{1}$$

where $$A = Z_3 \cos^2 2\gamma_3 \cot P + Z_{3t} \sin^2 2\gamma_3 / \sin Q$$

$$B = Z_3 \cos^2 2\gamma_3 / \sin P + Z_{3t} \sin^2 2\gamma_3 / \sin Q \tag{2}$$

where
$Z_4 = \rho_4 c_4 / \cos \theta_4$
$Z_3 = \rho c / \cos \theta_3$
$Z_{3t} = \rho b / \cos \gamma_3$
$P = 2\pi FD(c_4^2 - c^2 \sin^2 \theta_4)^{\frac{1}{2}}$
$Q = 2\pi FD(c_4^2 - b^2 \sin^2 \theta_4)^{\frac{1}{2}}$
$\rho_4$: density of couplant.

$c_4$: velocity of longitudinal wave in the couplant.
ρ: density of sample.
c: velocity of longitudinal wave in the sample.
b: velocity of shear wave in the sample.
$\theta_3$, $\gamma_3$: refraction angles of the longitudinal and shear waves determined by the Snell's law.
$\theta_4$: angle of incidence on sample which is an independent variable in this case (angle is variable from zero to half the lens aperture angle in the acoustic microscope).
F: frequency of acoustic wave (which appears as a product with the crack depth D so that the quantity FD can be taken as an independent variable).

Since "A" and "B" in the equation (2) are real numbers at all times, the magnitude of the reflectivity R is 1 at all times, and only the phase varies as a function of the angle of incidence according to the value of FD as shown in the graph of FIG. 2. In FIG. 2, the phase is shown over the range of −180° to +180°, and the graph is continuous. The curve shows 360-degree phase delay at several points. This is because the acoustic wave of this incidence angle excites a particular mode of Lamb waves propagating though the thin plate-like portion 3. In the particular case shown here (to be described later), the phase seems to be leading in the neighborhood of zero degree incidence angle. Actually, however, this merely represents a reduction in the delay for the initial phase of the zero degree incidence angle, which is −310°.

The intensity V of a reflected acoustic beam is calculated in terms of an integral of the reflectivity (eq. (1)) over the angle of incidence.

The result varies with the acoustic characteristics of the sample. Here, typical behaviors will be analyzed in connection wth soda-lime glass, steel and silicon nitride, these substances having different characteristics.

First, the result of numerical calculation assuming a lens with a half aperture angle of 60° is discussed. Table 1 shows the values of the density and longitudinal and shear wave velocities used for the calculation.

TABLE 1

| Substance | Density "ρ" | Longitudinal wave velocity "c" | Shear wave velocity "b" |
|---|---|---|---|
| Soda-lime glass | 2.5 (g/cm³) | 5821 (m/s) | 3359 (m/s) |
| Steel | 7.9 | 5950 | 3240 |
| Silicon nitride | 3.15 | 11400 | 6600 |

Table 2 shows the results of calculation of the values of thickness of plate-like portion that give minima of reflection intensity.

TABLE 2

| Substance | Position of minimum 1 | Position of minimum 2 | Position of minimum 3 |
|---|---|---|---|
| Soda-lime glass | 14 (μm) | 25 (μm) | 58 (μm) |
| Steel | 14 | — | — |
| Silicon nitride | 27 | — | — |

Frequency is 200 MHz. Half aperture angle of lens is 60°. Mark - means that no minimum is formed.

Table 3 shows the threshold thickness of substances with respect to Lamb waves.

TABLE 3

| Substance | ½ longitudinal wave wavelength | 3/2 shear wavelength | 2 longitudinal wave wavelength |
|---|---|---|---|
| Soda-lime glass | 14.5 (μm) | 25.2 (μm) | 58.2 (μm) |
| Steel | 14.9 | — | — |
| Silcon nitride | 28.5 | — | — |

Frequency is 200 MHz. Thickness values corresponding to the values in Table 2 are shown.

(1) Soda-lime glass

Figure 3A:
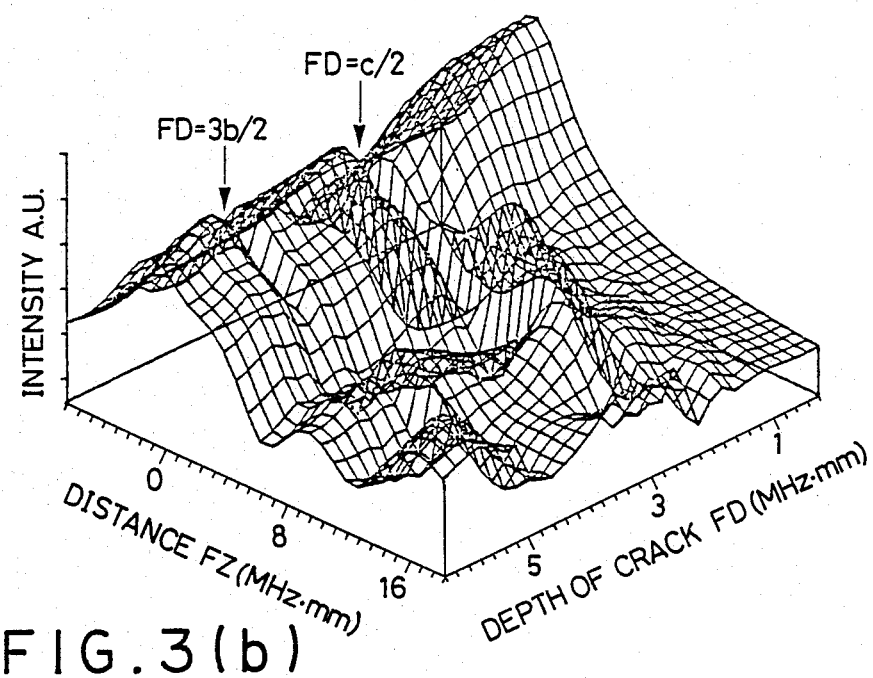
FIGS. 3(a) and 3(b) are graphs illustrating examples of calculation of the reflected wave intensity with soda-lime glass.
Figure 3B:
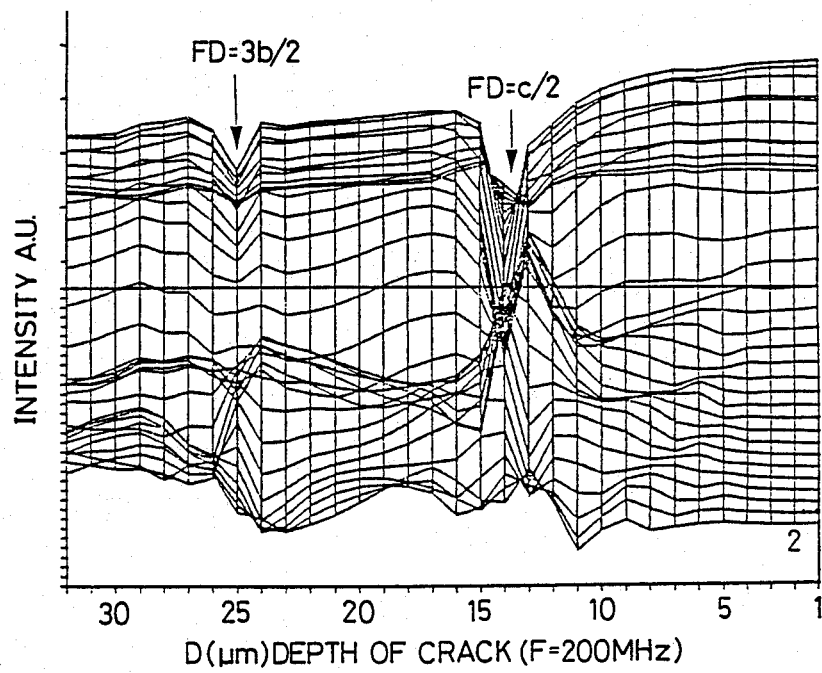

When the sample is soda-lime glass, the integral of the reflected wave intensity with respect to the incidence angle is given as functions of the distance z between the lens and sample surface and depth D of crack, as shown in FIGS. 3(a) and 3(b). In the Figures. the origin is taken such that the focal point is just on the surface of the sample. The direction of lens approach is defined as negative. The abscissa is scaled in units multiplied by the frequency F of the acoustic wave so as to provide greater generality.

Generally, when Z=0 the effect of acoustic characteristics of the sample is not manifested to much. In the cases of FIGS. 3(a) and 3(b), however, there are dips of minima at a particular depth of crack as shown by the mark ↓ and these dips are substantially parallel to the FZ axis.

This minimum will now be studied in further detail. FIG. 3(b) shows the results viewed in the direction of the FZ axis. In this graph, the abscissa is taken for D when F=200 MHz. In the illustrated range, there are minima at D=13 to 14 and D=25 μm. Calculation of higher values of D reveals that there are minimum intensities at values D as shown in Table 2.

(2) Steel

Figure 4:
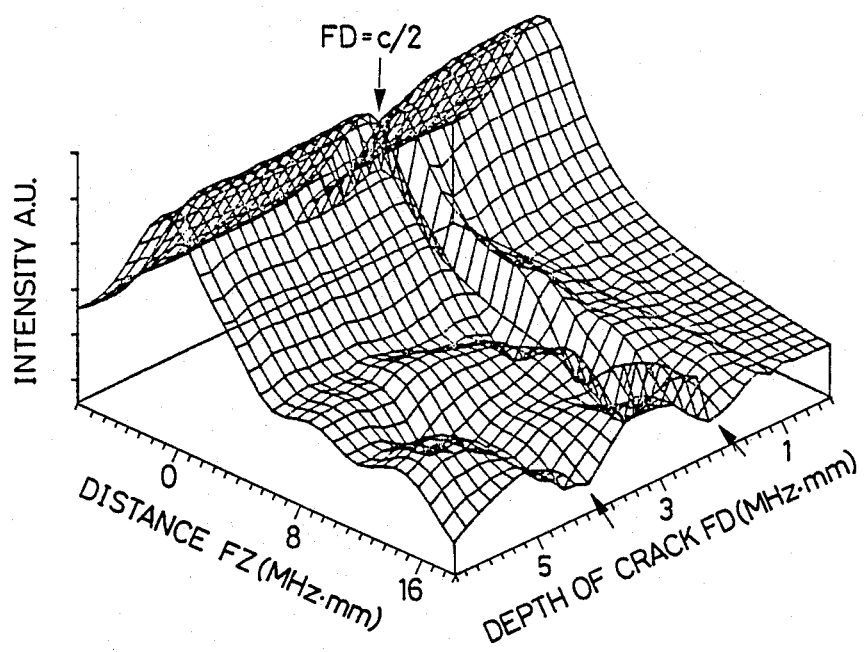
FIG. 4 is a graph illustrating an example of calculation of the reflected wave intensity with steel.

Steel, as shown in Table 1, does not differ so much from soda-lime glass in the sound velocities, but it differs greatly in density. This is reflected in the graph of FIG. 4. As shown in FIG. 4, the graph does not have the second minimum which is seen in the case of glass. Instead, with reduced values of FZ from −10 MHz mm, the first minimum is increased in width and also there is a wide second minimum.

(3) Silicon nitride

Figure 5A:
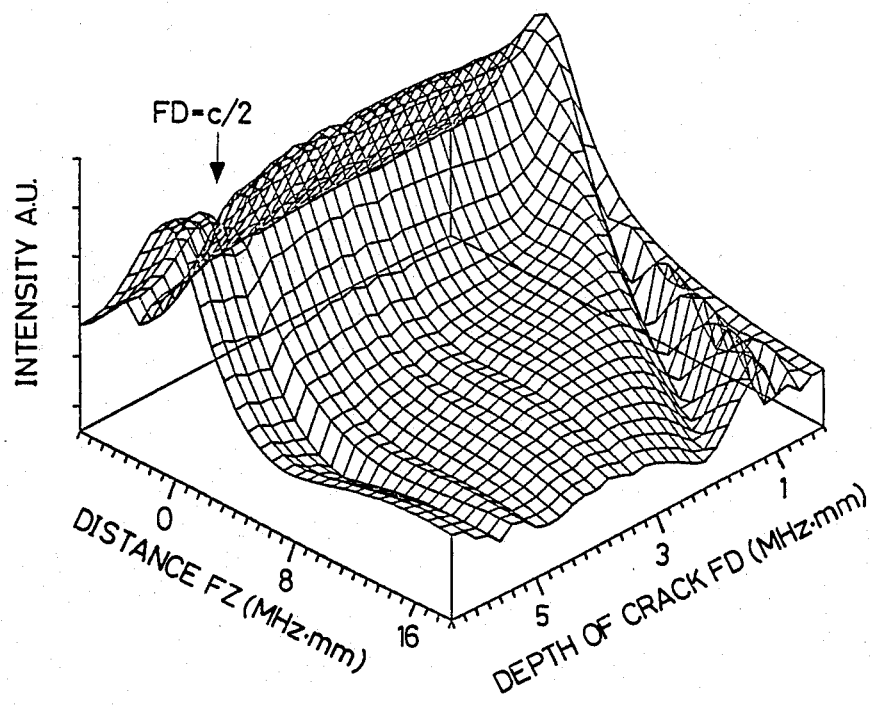
FIG. 5(a) is a graph illustrating an example of calculation of the reflected wave intensity with silicon nitride.
Figure 5B:
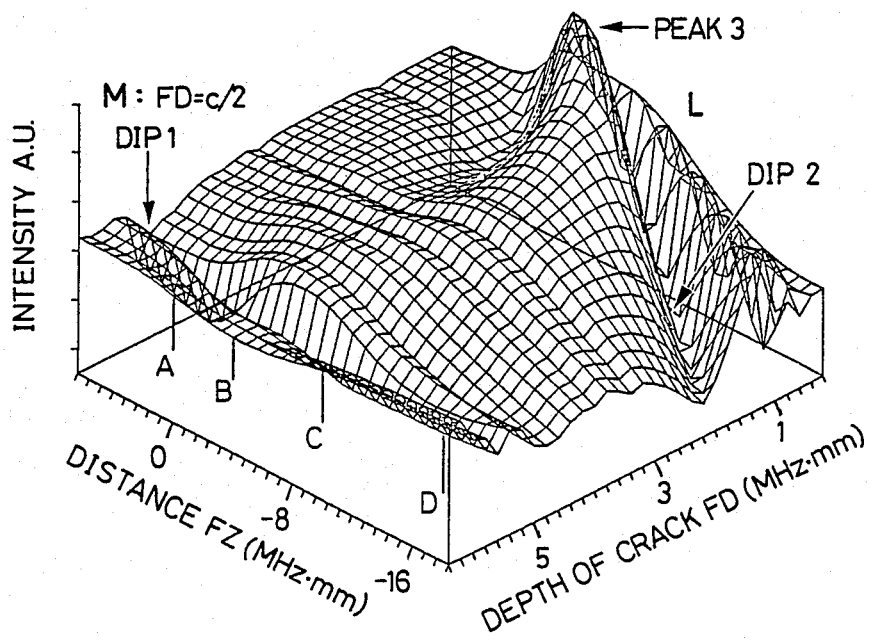
FIG. 5(b) is a graph illustrating an example of calculation of the reflected wave intensity by subtracting the intensity in a crack-free portion.

Lastly, silicon nitride will be considered as a typical material with large sound velocities. FIG. 5(a) shows the results of calculation. FIG. 5(b) shows results obtained by subtracting the intensity in the crack-free portion in order to clarify the difference in the brightness between the crack-free portion and the cracked portion.

The calculation results in this case are simple compared to the former two results and are characterized by a maximum (peak) and two minima (dips). Dip 2 is the first one of periodical minima in the Z axis direction, and it is a minimum of the usual V(z) curve. Its position reflects the velocity of leaky Lamb waves mainly in a zero order asymmetric mode AO, and its Z value is shifted towards zero with reduction of the crack depth, D.

Dip 1 at the position of FD=5.4 to 5.6 MHz mm is of the same character as those which have been heretofore observed.

From the above study it has become apparent that the results obtained by calculation in the method noted before can explain acoustic images of cracks in various substances in considerable detail.

The reduction of the reflected wave intensity with a crack is a peculiar phenomenon, and its mechanism has to be elucidated in order to utilize it for the measurement of the crack depth.

As shown in Table 2, the second and following position minima are observed with only soda-lime glass, while in silicon nitride and steel, only the first position minimum could be observed. Accordingly, the relation between the value of FD which gives a reflected wave intensity minimum and sound velocity of the material was studied, whereby it was found that there was a simple relation that $$FD \approx c/2, \text{ or } 3b/2 \tag{3}$$

as shown in Tables 2 and 3. Although this result is unexpected, it is obtainable by independently varying the longitudinal and shear wave velocities with the three different substances noted above and is also obtainable in a range of a few % by varying the half aperture of the lens up to approximately 30°. Therefore, it is thought to be a general principle.

The inventor has already found that the V(z) curve which represents the acoustic image of a crack is mostly prescribed by the lowest order, i.e., zero order, asymmetric mode of Lamb waves when the crack depth is small.

As is well known in the art, the Lamb waves have a symmetric mode, in which vibrations take place symmetrically with respect to the center line of a plate, and an asymmetric mode, in which vibrations are asymmetric. Each of these modes includes a zero order mode which constitutes a basic vibration and higher order modes constituting harmonics. Of these modes, in the first and higher order modes the sound velocity approaches the shear wave velocity when the thickness of the plate-like portion is infinite, while it diverges to infinity when the thickness is reduced and approaches the threshold thickness. For a Lamb wave in free space, the threshold thickness is one half of an integral multiple of the wavelength of the longitudinal or shear wave. This relation holds approximately even where the plate is in contact with a liquid. Therefore, the values of one half of an integral multiple of the wavelengths shown in Table 3 correspond to threshold plate thicknesses in certain modes of Lamb wave.

Figure 6:
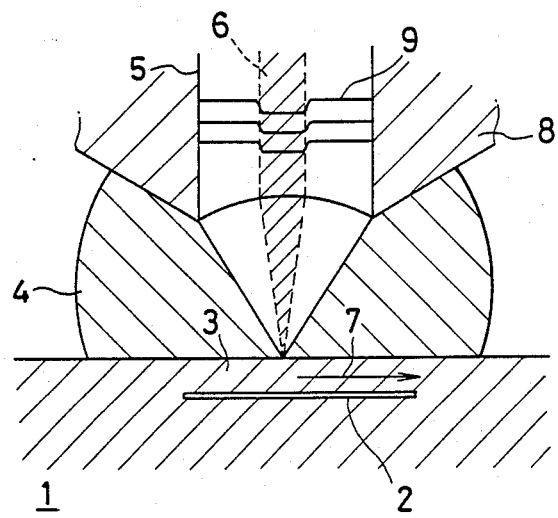
FIG. 6 is an explanatory view showing the method according to the present invention.

From the above fact, a model as shown in FIG. 6, is conceivable concerning the minimum of the reflected wave intensity. When the depth of the crack 2 in the sample 1 is equal to the threshold thickness of higher order modes of the Lamb wave, the velocity of the wave is extremely high. When such wave is excited with a wave 5 incident from the liquid 4, a shaded portion 6 of nearly perpendicular incidence in the reflected wave 9 makes a contribution. Meanwhile, when a Lamb wave 7 is excited, the boundary condition is changed, so that a phase delay of the reflected wave 9 occurs in this portion. In the neighborhood of Z=0 where a minimum is observed, the intensity of a wave component perpendicularly incident on the sample 1 is high. Therefore, the phase delay in this portion leads to a destructive interference with peripheral portions of the reflected wave of large incidence angles to reduce the total reflected wave intensity. Reference numeral 8 in the Figure designates an acoustic lens.

However, where the crack depth is different from the values shown in Table 2, the Lamb wave velocity in the sample is low, and consequently the wave is excited by an oblique component of the incident wave. The oblique component, however has low intensity in the neighborhood of Z=0, so that a phase delay of this component does not result in reduction of the reflected wave intensity. This is thought to be a cause of the reflected wave intensity minimum.

Now, a method of measurement according to the invention will be described specifically with reference to FIGS. 7 and 8.

Figure 7:
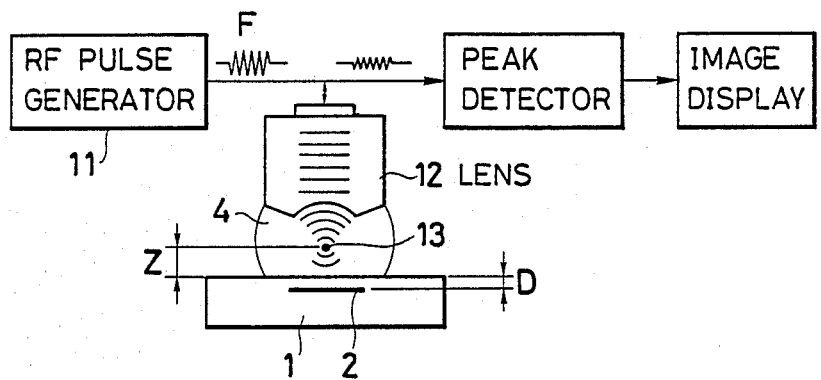
FIG. 7 is a block diagram showing an example of an apparatus for carrying out the method of measurement according to the invention.
Figure 8:
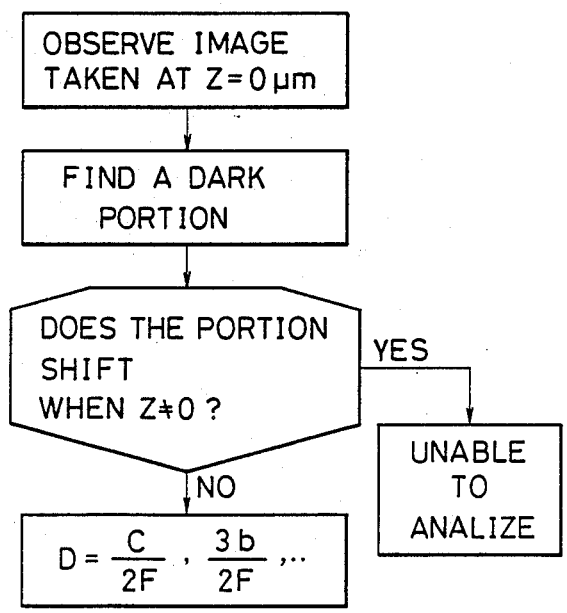
FIG. 8 is a flow chart showing the procedure of measurement according to the invention.

FIG. 7 shows an embodiment of the apparatus for carrying out the method of measurement of a microcrack depth according to the invention. A plane acoustic wave is generated according to a high frequency burst signal generated from an RF pulse generator 11, and it is converted by an acoustic lens 12 into a converging acoustic wave to be radiated onto a sample having a surface located at a position defocused by a distance z from a focal point 13. The resultant reflected wave from the sample is converted by the same lens 12 into a plane acoustic wave to be coupled to a peak detector 14 for peak detection. A two-dimensional distribution of the peak value is thus obtained and recorded to be displayed on an image display 15.

This operation is basically the same as the operation of the ordinary ultrasonic microscope operated above 100 MHz or an acoustic C scan imaging apparatus used at a lower frequency less than 20 MHz.

Next, the procedure of measuring of the crack depth using this apparatus will be described with reference to FIG. 8. A sample which is thought to have a crack is imaged at $Z=0$ μm, and a dark portion compared to the surroundings is searched for. Then, whether the dark portion can be horizontally displaced is checked by varying the distance between the lens and the sample slightly (less than three wavelengths in the coupler which is determined by the frequency). If a displacement takes place, the cause of the dark portion is not such a crack that can be dealt with by the method according to the invention. If the dark portion is not displaced, it is judged to be a portion of a crack nearly parallel to the sample surface. Then, according to eq. (1) the depth D takes a particular value among, c/2F and 3b/2F, where c and b are velocities of the longitudinal and shear waves in the sample, respectively, and F is the frequency of the acoustic wave.

It has to be determined using other information which one of the values obtained is correct. For example, where a crack is open on the sample surface, a dark portion closest to the opening corresponds to D=c/2F, which is a minimum value. Further, with steel or like material only a dark portion corresponding to c/2F appears due to the characteristics of the material, so that the possibility of others is excluded from the outset.

Further, by varying the frequency F of the acoustic wave, a dark portion can be observed at a different location, and the depth at that location can be obtained. By repeating this operation, the depth of various parts of the crack can be measured.

Now, an example of the invention will be described. Chipping crack of a bearing (SUJ 3) which had undergone extraordinary rupture was measured in liquefied butane using a 200-MHz acoustic microscope capable of measurement in a continuously variable frequency range.

Figure 9:
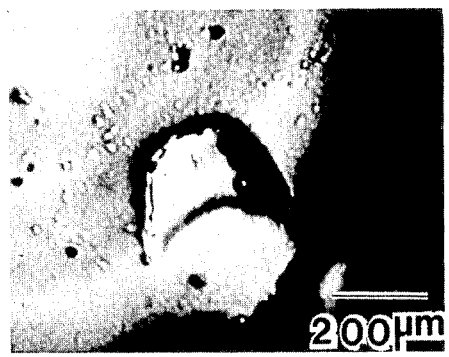
FIG. 9 is a photograph showing an acoustic image as an example of the measurement result.
Figure 10:
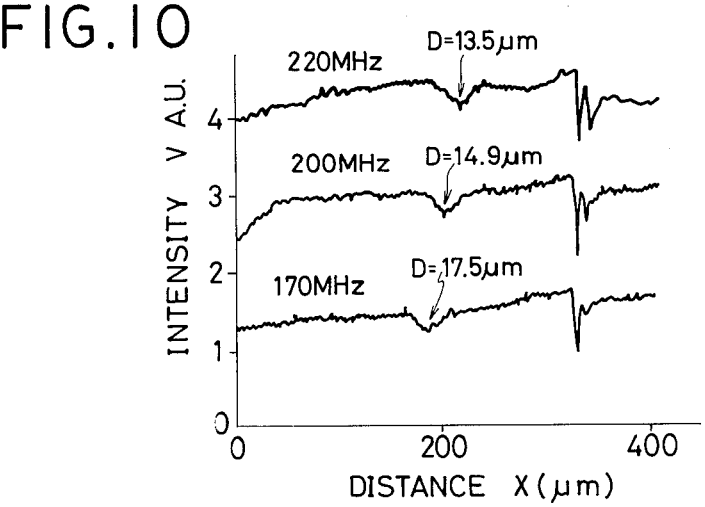
FIG. 10 is a graph showing the dependency on frequency of the position of minimum reflected wave intensity in a sample.

An acoustic wave at a frequency of 200 MHz was projected from the acoustic microscope onto the bearing which was set at the focal point. As a result, an acoustic image as shown in FIG. 9 was obtained. This acoustic image had a dark portion corresponding to a minimum at FD=c/2. The dark portion was measured by varying the frequency from 220 to 170 MHz. As a result, the dark portion was displaced as shown in FIG. 10. Arrows indicate the position of dark portions and the numerals indicate predicted depths.

Figure 11:
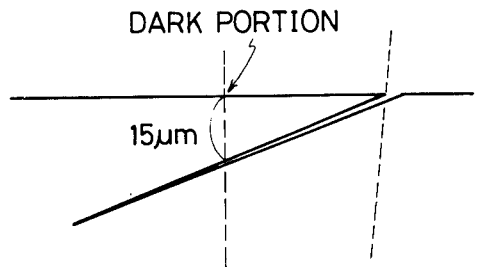
FIG. 11 is a sectional view showing a crack in a sample subjected to measurement.

The inside of the bearing was examined by grinding the bearing from the surface. As a result, it was found that the structure had a crack as shown in FIG. 11 and the depth of the dark portion was equal to a half wavelength of the longitudinal wave (approximately 15 μm at 200 MHz) with allowance of several microns. This result is consistant with the predicted depth in FIG. 10.

As has been described in the foregoing, according to the invention the crack depth is measured by setting the sampler in the neighborhood of the focal point of an acoustic beam, so that the depth can be measured with the same azimuth resolution as the acoustic image. Therefore, it is possible to measure microcracks of 10 μm or less using a commercially available acoustic microscope without need of additional equipment. Thus, the invention is very useful in practice.

Further, in the method according to the invention burst acoustic waves can be used, so that waves at frequencies up to 1 GHz or above may be used. This means that is is possible to measure smaller crack depths.

What is claimed is:

1. A method of measuring a depth of a microcrack substantially parallel to a surface of a sample comprising the steps of:

generating a tone burst of converging acoustic beam by using an acoustic lens with a half aperture angle of more than 20 degrees having its center line perpendicular to said surface, irradiating the sample placed in the neighborhood of a focal point of said acoustic beam;

exciting a leaky Lamb wave with phase velocity greater than 10,000 m/s by a portion of nearly perpendicular incidence, leading to a destructive interference with peripheral portions of the beam;

detecting any peaks of the reflected beam from the sample and checking whether the reflected beam intensity assumes a minimum value.

* * * * *